United States Patent [19]

Freda et al.

[11] Patent Number: 4,596,249

[45] Date of Patent: Jun. 24, 1986

[54] IMPLEMENT FOR SETTING SUTURES

[76] Inventors: Vincent J. Freda, Robin La., Alpine, N.J. 07620; Henry Puchalski, 234 4th St., Palisade Park, N.J. 07650

[21] Appl. No.: 517,276

[22] Filed: Jul. 26, 1983

[51] Int. Cl.[4] .............................................. A61B 17/04
[52] U.S. Cl. ................................. 128/334 R; 128/340
[58] Field of Search ................... 128/334 R, 326, 340, 128/339, 335.5

[56] References Cited

U.S. PATENT DOCUMENTS

| | | | |
|---|---|---|---|
| 1,635,066 | 7/1927 | Wells | 128/334 R |
| 1,815,725 | 7/1931 | Pilling et al. | 128/334 R |
| 1,856,721 | 5/1932 | Nagelmann | 128/334 R |
| 1,933,024 | 10/1933 | Nagelmann | 128/334 R |
| 2,895,478 | 7/1959 | Post | 128/334 R |
| 3,470,875 | 10/1969 | Johnson | 128/334 R |
| 3,842,840 | 10/1974 | Schweizer | 128/334 R |
| 4,373,530 | 2/1983 | Kilejian | 128/334 R |
| 4,423,729 | 1/1984 | Gray | 128/334 R |

Primary Examiner—Gene Mancene
Assistant Examiner—James Hakomaki
Attorney, Agent, or Firm—William L. Botjer

[57] ABSTRACT

An implement for setting sutures particularly suitable for use in situations where access to the tissue to be sutured is difficult. The implement includes a pair of hinged arms, each having a handle portion and a jaw portion. The tip of one jaw has a tissue piercing hook and the tip of the other jaw has a notch or opening through which the hook may pass. A series of guides and openings position the suture above the opening for engagement by the hook. When the jaws are closed about the tissue, the hook will pass through the tissue and the suture will ride around the hook. The suture will be engaged by the hook and upon opening the jaws, the hook will pull a loop of suture through the tissue, the loop may then be cut and the suture fixed in the usual manner.

5 Claims, 4 Drawing Figures

IMPLEMENT FOR SETTING SUTURES

BACKGROUND OF THE INVENTION

This invention relates generally to a implement for setting sutures for use in surgery, which is particularly suitable for setting sutures in locations that are difficult to reach.

Upon the completion of surgery it is standard procedure to sew up the surgical incision by using a suture or clamp. In common practice, the surgeon threads a small needle and thereafter clamps the needle in the jaws of a surgical clamp. The clamp and needle are then manipulated into the desired position and the suture is set. While this conventional procedure is adequate for some procedures in easily accessible parts of the body, it is difficult, and of times dangerous, to use in certain inaccessible areas, such as during a vaginal hysterectomy. During the procedure the needle could slip or move in the jaw of the clamp, which could prevent the suture from being properly positioned, or even worse, the needle may be dislodged from the clamp and have to be removed.

It is thus an object of the present invention to overcome these problems by providing a one-piece surgical tool for setting a suture, without difficulty, in hard to reach places.

It is a more general object of this invention to provide an improved implement for setting sutures.

It is a further object of this invention to provide an implement for setting sutures in hard to reach locations.

It is yet a further object of this invention to provide an implement for setting sutures that provides a high degree of accuracy in placement.

SUMMARY OF THE INVENTION

The invention is directed to a implement for setting sutures in hard-to-reach places. The implement includes a pair of hinged arms, each having a handle portion and a jaw portion. The jaw of one arm includes a piercing hook and the jaw of the other arm includes a notch or opening through which the piercing hook may pass. The suture is fixed to one arm and a series of guides dispose the suture across the opening in the jaw. The tissue in which the suture is to be placed is then disposed between the jaws and the jaws are closed. The piercing hook can penetrate and pass through the tissue and thereafter contact the suture. The suture will then ride over the top of the hook and be grasped in the curve of the hook. As the jaws are opened the hook will pull a loop of suture through the tissue, which may then be cut and tied in the usual manner.

DESCRIPTION OF THE DRAWINGS

For a fuller understanding of the invention, reference is had to the following description taken in connection with the accompanying drawings of the preferred embodiment in which.

DESCRIPTION OF THE PREFERRED EMBODIMENT

Figure 1:
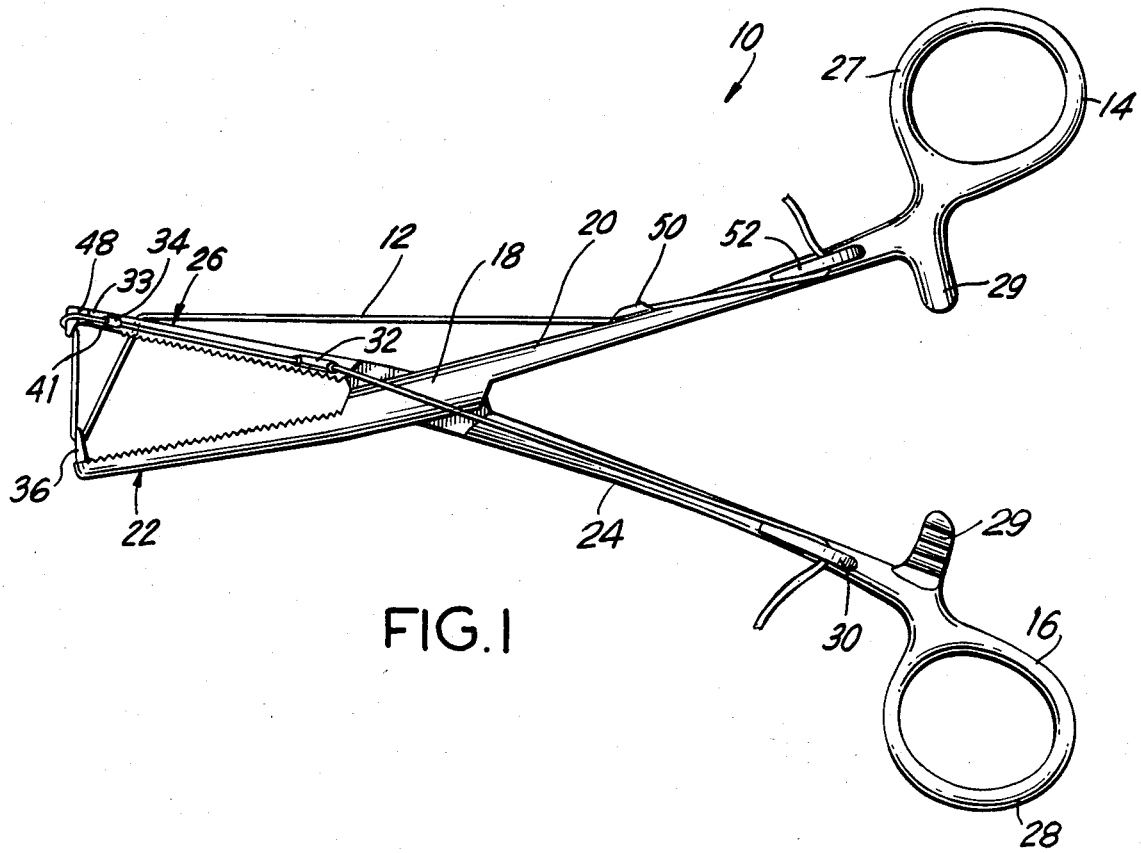
FIG. 1 is a plan view of the suture setting implement of the present invention with the jaws shown in the open position.

The drawings illustrate a implement 10 for setting a suture 12. Implement 10 resembles the usual surgical clamp or hemostat and is comprised of two arms 14 and 16 which are pivotally joined together about a hinge 18. Arm 14 includes a handle 20, a jaw 22, and a finger loop 24 disposed at one end of handle 20. Similarly, arm 16 includes a handle 24, a jaw 26 and a finger loop 28. Arms 14, 16 may also include interengaging toothed extensions 29 for locking arms 14, 16 in the closed position. It is to be noted that the size, proportions and lengths of the various elements of implement 10 may be changed to suit any particular surgical requirements.

Handle portion 24 of arm 16 includes a spring clamp 30 in the form of a leaf spring to which one end of suture 12 is fixed by wedging a portion of suture 12 under spring clamp 30. Clamp 30 may be replaced by any suitable means for fixing suture 12 to handle portion 24 of arm 16. The side of jaw 26 of arm 16 includes tubular guides 32, 34 through which suture 12 is threaded.

Figures 2A, 2B:
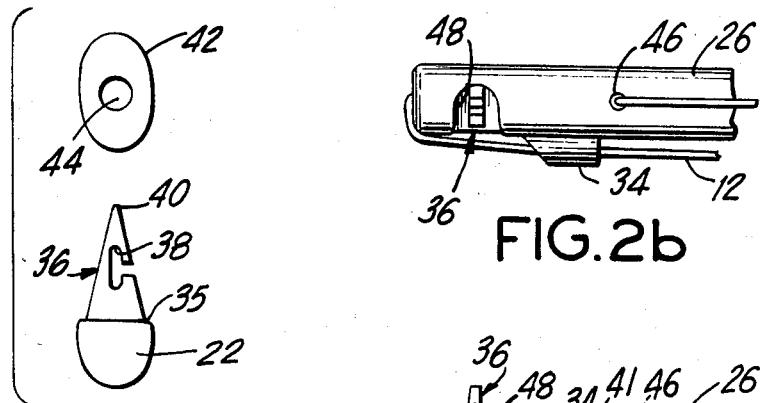
FIG. 2a is a detailed view of the tip of the jaws as seen from the front with the jaws open.
FIG. 2b is a detailed view from the top of the upper jaw of the implement.
Figure 2C:
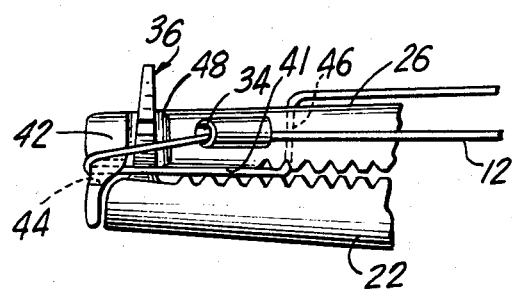
FIG. 2c is a detailed side view of the jaws in the closed position.

FIGS. 2a, 2b and 2c illustrate in detail the tips of jaws 22, 26 of arms 14, 16. Extending perpendicularly from the inner face 35 of jaw 22 of arm 14 is a tissue piercing hook 36. Hook 36 includes a concave inner surface 38 and a pointed or sharpened outer surface 40. Hook 36 is disposed on face 35 of jaw 22 slightly offset from the centerline of jaw 22 so that suture 12 will be directed toward the open side of hook 36.

Jaw 26 of arm 16 includes an opening or notch 48 through which hook 36 will pass when the jaws are closed. It is noted that hook 36 extends beyond the upper surface 33 of jaw 26 when the jaws are closed. As is seen in FIG. 2c, jaw 26 is longer than jaw 22. Extending perpendicularly from the end of inner face 41 of jaw 26 is a projection 42 having an opening 44 through which suture 12 passes. Jaw 26 includes an opening 46 extending from inner face 41 to upper surface 33 through which suture 12 may be threaded. Handle portion 20 of arm 14 includes a tubular guide 50 and another spring clamp 52. One end of suture 12, inserted under clamp 30, is passed through tubular guides 32 and 34 and is then inserted in opening 44 in projection 42 from the outer side. Suture 12 then is threaded through opening 46, tubular guide 50 and the free end of suture 12 is then fixed at clamp 52.

In use, the free ends of suture 12 are secured under spring clamps 30 and 52, the portion of the tissue to be sutured is placed between jaws 22, 26, and finger loops 24, 28 are brought together to close the jaws. Hook 36 will then penetrate the tissue and exit its other side. As upper surface 40 of hook 36 approaches suture 12, suture 12 will slide along surface 40 towards the open side of hook 36 and then be engaged by inner concave surface 38 of hook 36. When jaws 22, 26 are opened, suture 12 will be engaged by hook 36 and withdrawn through the tissue, thus pulling a loop of suture 12 through the tissue as shown in FIG. 1. Thereafter suture 12 may be cut and set in the usual manner.

Although the present invention has been described in conjunction with the preferred embodiment, it is to be understood that modifications and variations may be resorted to without departing from the spirit and scope of the invention as those skilled in the art will readily understand. Such modifications and variations are considered to be within the purview and scope of the invention and the appended claims.

What is claimed is:

1. An implement for setting a suture in tissue, said implement comprising:
   (a) first and second hinged arms, each arm defining a handle portion and a jaw portion;
   (b) said jaw portion of said first arm having a opening therein;
   (c) said jaw portion of said second arm including a hook constructed and arranged to pierce tissue and being sized to pass through said opening of said jaw portion of said first arm when the jaws are closed;
   (d) suture positioning means disposed on at least one of said first and second arms; said positioning means disposing a portion of said suture proximate said opening in said jaw portion of said first arm;
   (e) said positioning means including an opening disposed between the inner and outer surfaces of said first arm, a projection disposed at the tip of said first arm extending perpendicularly from said jaw portion of said first arm and having an aperture therein, and tubular means disposed on the said of the jaw portion of said opening of said first arm, said positioning means permitting said suture to be threaded through said opening disposed between the inner and outer surfaces of said first arm, through said opening in said projection and thereafter through said tubular means to thereby securely position said suture for engagement with said hook; and
   (f) said hook piercing said tissue when said jaws are closed, said hook passing through said tissue and said hook engaging said portion of said suture disposed proximate said opening, upon the opening of said jaws said hook retracting a loop of said suture through the opening pierced in said tissue.

2. The implement as claimed in claim 1 wherein said handle portions of at least one of said first and second arms include means for fixing one end of said suture thereto.

3. The implement as claimed in claim 2 wherein said means for fixing one end of said suture include a flexible leaf clamp under which a portion of said suture may be wedged.

4. The implement as claimed in claim 1 wherein said guide means for said suture includes tubular means disposed on at least one of said first and said second arms.

5. The implement as claimed in claim 1 wherein said tissue piercing hook includes a tissue piercing upper surface and a concave lower surface.

* * * * *